United States Patent [19]  
Sofianos et al.

[11] Patent Number: 5,627,295  
[45] Date of Patent: May 6, 1997

[54] SYNTHESIS OF HIGHER ALCOHOLS

[75] Inventors: Alkeos Sofianos; Michael S. Scurrell, both of Pretoria, South Africa

[73] Assignee: Patlico International BV, Rotterdam, Netherlands

[21] Appl. No.: 215,199

[22] Filed: Mar. 21, 1994

[30] Foreign Application Priority Data

Mar. 19, 1993 [ZA] South Africa ............ 93/1979

[51] Int. Cl.$^6$ .................................... B01J 23/80
[52] U.S. Cl. ............................ 556/27; 556/31
[58] Field of Search ........................ 556/27, 31

[56] References Cited

U.S. PATENT DOCUMENTS 5,254,520 10/1993 Sofianos .................. 502/307

FOREIGN PATENT DOCUMENTS 0482753 4/1992 European Pat. Off. .
89/1295 2/1989 South Africa .

Primary Examiner—Johann Richter
Assistant Examiner—John Peabody
Attorney, Agent, or Firm—Ladas & Parry

[57] ABSTRACT

A higher alcohol synthesis catalyst precursor comprises a homogeneous, highly crystalline, hydroxycarbonate compound containing copper, zinc and at least one element selected from the group consisting of aluminium, manganese and chromium. It also comprises at least one element from at least one of the followng groups of the Periodic Table of Elements: Group IIIA, Group IIIB, Group IVB and Group VIIB.

9 Claims, 4 Drawing Sheets

SYNTHESIS OF HIGHER ALCOHOLS

This invention relates to the synthesis of higher alcohols. It relates in particular to a higher alcohol synthesis catalyst precursor, to a method of forming a higher alcohol synthesis catalyst precursor, to a higher alcohol synthesis catalyst and method of making thereof, and to a process of higher alcohol synthesis.

According to a first aspect of the invention, there is provided a higher alcohol synthesis catalyst precursor, which comprises a homogeneous, highly crystalline, hydroxycarbonate compound containing copper, zinc and at least one element selected from the group consisting of aluminium, manganese and chromium; and at least one element from at least one of the following groups of the Periodic Table of Elements: Group IIIA, Group IIIB, Group IVB and Group VIIB.

By 'highly crystalline' is meant that the compound is composed of a group of atoms arranged in a regular and repeated pattern, and forming a homogeneous, anisotropic body having the natural shape of a polyhedron. This definition is supported by Klug and Alexander, 'X-ray Diffraction Procedures', a Wiley-Interscience Publication, John Wiley, New York, 1974, page 3.

By 'higher alcohol' is meant an alcohol or alcohols having more than one carbon atoms, ie other than methanol, such as ethanol, 1-propanol, isobutanol, tertiary butyl alcohol, or the like. However, when a catalyst formed from such a precursor as hereinafter described is used for alcohol synthesis as hereinafter described, it is to be appreciated that methanol can then also be synthesized simultaneously with the higher alcohol(s).

The Periodic Table of Elements referred to is that in general usage. For example, it can be that depicted on page 21 of Volume 10 of McGraw-Hill Encyclopedia of Science and Technology, 5th Edition, published in 1982 by McGraw-Hill Book Company.

The hydroxycarbonate compound may have a hydrotalcite-type structure, ie having the general formula $Cu_xZn_{(6-x)}M_2(OH)_{16}CO_3 \cdot 4H_2O$, where M is Cr or Al. The atomic ratio of [Cu+Zn]:M therein may be between 2:1 and 4:1, preferably between 2.75:1 and 3.25:1. In addition, the atomic ratio of Cu:Zn therein may be between 0.4:1 and 1.2:1, preferably between 0.5:1 and 1:1.

Instead, the hydroxycarbonate compound may have a binary aurichalcite-type structure, ie having the general formula $(Cu_xZn_{1-x})_5(CO_3)_2(OH)_6$, with the atomic ratio of Cu:Zn therein being between 0.4:1 and 1.2:1, preferably between 0.5:1 and 1:1.

The element of Group IVB may be present, and may be titanium, zirconium or hafnium. Instead, or additionally, the element of Group VIIB may be present, and may be manganese. Instead, or additionally, the element of Group IIIA may be present, and may be indium. Instead, or additionally, the element of Group IIIB may be present, and may be lanthanum.

In one embodiment of the invention, the element of Group IVB and/or VIIB may be incorporated into the crystal lattice of the hydroxycarbonate compound, replacing, for example, in the case of manganese, some of the aluminium or chromium in the hydrotalcite structure. Zirconium and the other elements of Group IVB can also, at least to some extent, be incorporated in the crystalline lattice, but can also, or instead, provide a zirconia matrix around and between the hydroxycarbonate crystals.

In another embodiment of the invention, the precursor may comprise a homogeneous mixture of two phases, with the one phase being crystalline and comprising a ternary hydrotalcite-like compound as hereinbefore described, and the other phase being an amorphous phase comprising a solid mixture of zirconia and/or mangania and/or lanthana and/or india.

In yet another embodiment of the invention, the precursor may comprise an intimate mixture of two phases, with the one phase being crystalline and comprising a binary aurichalcite-type hydroxycarbonate compound of the general formula $(Cu_xZn_{1-x})_5(CO_3)_2(OH)_6$ as hereinbefore described, and the other phase comprising a solid mixture of mixed oxides of zirconium and/or manganese and/or lanthanum and/or indium.

The element of Group IIIA, Group IIIB, Group IVB and/or Group VIIB may be present, in the precursor, in the form of its carbonate or any other salt which is thermally decomposable to oxides or mixed oxides.

Where a precipitation reactor is used, the reactor vessel will thus naturally be allowed to stand under stirring as hereinbefore described. The separation may be effected by filtration.

According to a second aspect of the invention, there is provided a method of forming a higher alcohol synthesis catalyst precursor, which method comprises forming a precipitate comprising compound(s), thermally decomposable to oxide(s) or mixed oxide(s), of copper, zinc, at least one element selected from the group consisting of aluminium, manganese and chromium, and at least one element from at least one of the following groups of the Periodic Table of Elements: Group IIIA, Group IIIB, Group IVB and Group VIIB, the precipitate comprising at least a homogeneous highly crystalline hydroxycarbonate compound.

In one version, the precipitate may be formed on a batch basis. The formation of the precipitate may be effected by admixing solutions of the compounds, which may, for example, be carbonates; heating the resultant mixture to its precipitation temperature; heating a solution of a precipitant in water; and thereafter adding both hot solutions to preheated demineralized water with vigorous stirring and strict pH control, eg in a precipitation reactor.

Instead, the formation of the precipitate may be effected by admixing solutions of the compounds; heating the resultant mixture to its precipitation temperature; and adding the preheated mixture of compounds rapidly to a predetermined or controlled volume of a preheated solution of a precipitant in water.

Instead, the formulation of the precipitate may be effected by admixing solutions of the compounds of the elements; heating the resultant mixture to its precipitation temperature; and adding a solution of precipitant in water, preheated to a predetermined precipitation temperature, to the hot solution of mixture of the compounds, while stirring vigorously, until a predetermined pH value of the hot solution or mixture to which the precipitant solution is added, is reached.

The method may include separating the precipitate from the residual liquid after allowing the liquid to stand under stirring and at the precipitation temperature for a period of time, eg for between 0.5 and 60 minutes, for aging of the catalyst precursor. Where a precipitation reactor is used, the reactor vessel will thus naturally be allowed to stand under stirring as hereinbefore described. The separation may be effected by filtration.

The method may include resuspending the precipitate at least once, but typically 2 to 4 times, in demineralized water, separating it from the water by filtration, and finally washing it thoroughly to remove as much alkali metal as possible. If necessary, an ion-exchange of the residual alkali ions against ammonium ions can be carried out in order to remove all alkali ions.

The precipitant may be a solution of sodium, potassium and/or ammonium carbonate or bicarbonate in water.

The precipitation may be carried out in a broad temperature range, eg between about 40° C. and 100° C. Lower temperatures, eg between about 50° C. and 60° C. are preferred, so that the crystalline size of the catalyst precursor so formed is larger. The precipitation may be effected at a pH in the range of 6,5–10, and preferably between 8 and 9.

The washed precipitate comprising a homogeneous hydrated hydroxy carbonate precursor, or a homogeneous mixture thereof with a gel comprising a mixture of zirconia and mangania, may then be dried by any known drying process, for example in an oven at temperatures between 30° C. and 130° C., under vacuum or at normal pressure. Alternatively spray drying may be employed.

In another version of the invention, the precipitate may be formed by admixing solutions of the compounds; heating the resultant mixture of solutions to its precipitation temperature; heating a solution of the precipitant in water to the precipitation temperature; adding, eg feeding, the two solutions simultaneously to a first stirred reactor containing demineralized water preheated to the precipitation temperature under strict pH control; allowing the solutions to remain in the first reactor for a predetermined residence time, eg about 15 minutes, while precipitation occurs; transferring the contents of the first reactor via an overflow to a second stirred reactor in which the precipitate is allowed to mature or age for a predetermined period of time, eg about 60 minutes, and separating the aged precipitate from the residual liquid, as hereinbefore described.

If desired, the method may include feeding the solutions continuously to the first reactor, with the first reactor being shaped and dimensioned to provide the required or predetermined residence time, withdrawing precipitate containing solution continuously from the first reactor to the second reactor, and withdrawing aged precipitate continuously from the second reactor which will thus be shaped and sized accordingly to achieve the predetermined maturing time therein.

The first reactor may comprise a tubular reaction chamber having an inlet for the solution at or near its lower end, and an outlet near its upper end for withdrawing precipitate containing solution therefrom; and an elongate stirrer extending along the reaction chamber and having a plurality of longitudinally staggered blades. The chamber will thus be of sufficient length to obtain the predetermined residence time therein.

The stirrer may be located axially within the chamber, and the length of blades may be such that the diameter of the impeller is about half the diameter of the reaction chamber. The reactor may include heating means for heating the reaction chamber. The heating means may comprise a hot water jacket around the reaction chamber.

The invention extends also to a higher alcohol synthesis catalyst precursor formation reactor as hereinbefore described.

The invention extends also to a higher alcohol synthesis catalyst precursor, when formed by the method of the second aspect of the invention.

According to a third aspect of the invention, there is provided a method of making a higher alcohol synthesis catalyst, which comprises calcining a precursor as hereinbefore described.

The calcination may be effected by treating the precursor at a temperature of between 200° C. and 550° C., for between 3 and 10 hours, to obtain a homogeneous catalyst. When the precursor contains chromium, the calcination may be effected at temperatures of 250° C. to 400° C., and preferably between 300° C. and 375° C., while when it contains aluminium, it may be effected at temperatures of 400° C. to 550° C., particularly 425° C. to 500° C. The calcination must thus be effected at sufficiently high temperature for the conversion of the precursor to spinells, such as $CuAl_2O$, to occur irreversibly. If such irreversible spinell formation does not take place, then at the hydrothermal conditions under which the catalyst is used for the production of higher alcohols as hereinbefore described, the hydrotalcite phase would tend to reform, with resultant poor catalyst performance.

The calcination may instead, or additionally, be effected under a nitrogen atmosphere, eg in an oven, and using a temperature program to reach the desired calcination temperature. The calcination may thus be effected in a nitrogen stream, which typically has a flow rate of about 30 ml per minute. The heating rate of the oven can be between 1° C. and 5° C./min. Such calcination leads to a catalyst with good textural properties, eg higher surface area and high pore volume.

The method may include alkali metal promoting the calcined catalyst. Thus, it may contain, in admixture with the mixed oxide obtained through the calcination of the hydroxycarbonate compound, a minor proportion of an alkali metal oxide. The alkali metal oxide is obtained after a well determined amount of an alkali metal compound in aqueous solution or dissolved in a suitable organic solvent is impregnated in the calcined catalyst and then, after drying, decomposed by further calcination of the catalyst. The alkali metal compound may be a carbonate, acetate, formate, or other decomposable salt, and the alkali metal may be sodium, potassium or cesium. The catalyst may contain no more than 10% by mass of the alkali metal compound, and preferably about 1–5% by mass thereof.

The invention extends to a higher alcohol synthesis catalyst, when formed by the method as hereinbefore described.

According to a fourth aspect of the invention, there is a process of higher alcohol synthesis, which comprises reacting hydrogen and carbon monoxide and/or carbon dioxide in the presence of a higher alcohol synthesis catalyst as hereinbefore described, and at elevated temperature and pressure.

The reaction may be effected at temperatures of 275° C. to 350° C., and at a pressure of about 10 MPa. The hydrogen and carbon monoxide/dioxide may be part of a feed gas stream typically comprising, on a volume basis, 1%, $CO_2$, 47% CO, 5% argon and the balance hydrogen.

The invention will now be described by way of example with reference to the accompanying diagrammatic drawings.

Figure 1:
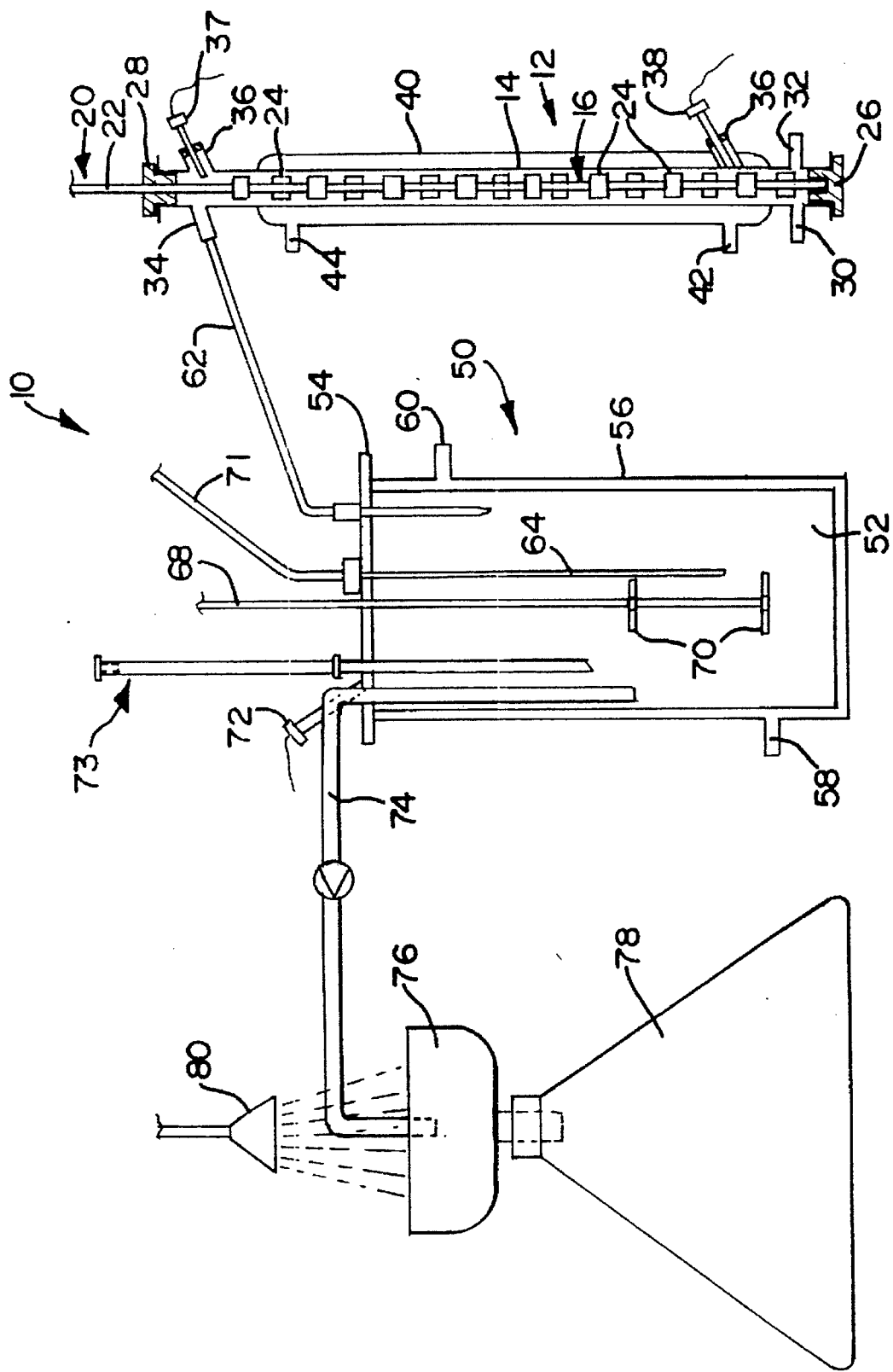
FIG. 1 shows, diagrammatically, bench scale apparatus for preparing a higher alcohol synthesis catalyst precursor, according to the invention.

Referring to FIG. 1, reference numeral 10 generally indicates bench scale apparatus for preparing or synthesizing higher alcohol synthesis catalyst precursors according to the invention.

The apparatus 10 includes a first reactor, generally indicated by reference numeral 12.

The reactor 12 comprises an upright central tube 14, typically having a diameter of about 24 mm, defining an elongate reaction chamber 16. An impeller or stirrer, generally indicated by reference numeral 20, extends axially along the tube 14. The impeller 20 comprises a rotatable shaft 22 connected to suitable drive means (not shown) such as an electric motor or the like. Square blades 24 are staggered longitudinally along the shaft 22. Typically, the size of the blades 24 is 12 mm×12 mm.

The lower end of the tube 14 is closed off with a Teflon (trade mark) closure 26, with the lower end of the shaft 22 being rotatably mounted within a recess in the closure 26. The upper end of the tube is closed off with a Teflon closure 28 having a central opening through which the shaft 22 passes. A metal salt solution inlet 30 is provided at the lower end of the tube 14, as is an alkali carbonate solution feed inlet 32. A slurry exit 34 is provided at the upper end of the tube.

The tube 14 also has components 36 fitted with pH and temperature monitors 37 and 38 respectively.

A hot water jacket 40, having a hot water inlet 42 at its lower end and a water outlet 44 at its upper end, is provided around the tube 14. The inlet 42 and outlet 44 are connected to a thermostatically controlled water heating means, as well as water circulating means. In this fashion, hot water, at a predetermined temperature, can be circulated through the jacket 40, thereby to heat up the reaction chamber 16 to this temperature. Typically, the jacket 40 has a diameter of about 48 mm.

The apparatus 40 also includes a second reactor, generally indicated by reference numeral 50, arranged cascade fashion with respect to the first reactor 12.

The reactor 50 comprises a cylindrical vessel 52 closed at its lower end and open at its upper end with a lid 54 closing off its upper end. A hot water jacket 56, similar to the hot water jacket 40, is provided around the vessel 52. The jacket 56 has a hot water inlet 58, as well as a water outlet 60.

A conduit 62 leads from the slurry exit 34 of the reactor 12 through the lid 54 into the vessel 52.

A thermostat 64 is also located in the reactor 50, as is a rotatable stirrer 68 having blades 70. A pH monitor 72 also extends into the vessel 52. The temperature is also strictly monitored with a temperature probe 71, and the vessel lid is also provided with a cooler 73.

A tube 74 leads from the vessel 52 to a large Buchner funnel 76 fitted to an evacuated flask 78. The funnel 76 is lined with suitable filter paper (not shown). Wash means 80 for washing residue which collect on the filter paper is provided above the filter 76.

In use, a metal salt solution as hereinafter described as well as a potassium or sodium carbonate solution are simultaneously fed via the inlets 30, 32 respectively into the bottom of the reaction chamber 16 of the first reactor 12. The feed rates are such that the residence time of the mixture in the reaction chamber 16 is about 15 minutes. A precipitate forms immediately, and by virtue of the construction of the reactor 12, all precipitate particles are subjected to substantially the same residence time in the reactor 12, thus ensuring homogeneity of the precursor.

A slurry of precipitate and spent solution passes, by means of the outlet 34 and the tube 62, into the reactor 50 where the precipitate is aged for about 60 minutes. The vessel 52 is thus sized to obtain the aging or maturation time of 60 minutes. Maturation or aging is effected at the same temperature as that at which the reactor 12 is maintained, under stirring.

Overflow from the reactor 50, comprising aged precipitate and spent solution passes, via the tube 74, to the funnel 76 with spent solution then passing into the vessel 78. The precipitate is washed as hereinafter described, utilizing the wash means 80.

Use of the reactors 12, 50 allows a strict maintenance of residence times of the crystallized particles in the reactors 12, 50 so that substantially all particles have the same residence times. This in turn promotes homogeity and crystallinity.

EXAMPLE 1

Preparation of Catalyst A 400 g chromium nitrate, $Cr(NO_3)_3.9H_2O$, were dissolved, in a first flask, in 1 l demineralized water to form a 1M solution (solution A). Similarly, in a second flask, 241,6 g of copper nitrate, $Cu(NO_3)_2.6H_2O$, were dissolved in 1 l demineralized water to form a 1M solution (solution B). In the same way, 297,48 g zinc nitrate, $Zn(NO_3)_2.6H_2O$, were dissolved in 1 l demineralized water to produce a 1M solution (solution C). Finally a solution of $Zr(NO_3)_4$ (solution D) and a solution of $Mn(NO_3)_2$ (solution E) were prepared by dissolving these salts in demineralized water (see Table 1). An aqueous 10% solution of potassium carbonate, $K_2CO_3$, was produced by dissolving 500 g of the salt in 5 l demineralized water (solution F).

The necessary quantities of solutions A to E as reflected in Table 1 were thoroughly mixed together to form solution F, and heated to 60° C. A quantity of about 2 l of the 10% $K_2CO_3$ is also heated, separately, to 60° C.

TABLE 1

| | Sample volume taken | Atomic Ratio |
| --- | --- | --- |
| $Cr_2O_3$ | 115 ml of 0,0520 g/ml Cr solution (A) | 6 |
| CuO | 102 ml of 0,07955 g/ml Cu solution (B) | 6,50 |
| ZnO | 149 ml of 0,08137 g/ml Zn solution (C) | 9,75 |
| $ZrO_2$ | 42 ml of 0,01453 g/ml Zr solution (D) | 1,25 |
| MnO | 18 ml of 0,03547 g/ml Mn solution (E) | 0,50 |

As first and second reactors, 5 l stirred vessels (not shown) instead of the reactors 12 and 50, and arranged cascade fashion, were used. The vessels were fitted with suitable heating elements, eg hot water jackets, and pumps.

At all time strict control of temperature, pH and stirring speed were maintained.

Prior to feeding solutions F and G into the first reactor, 250 ml demineralized water and 250 ml of a 10% potassium acetate solution were added to each of the reactors, and preheated to 60° C. At 60° C. the pH was then adjusted to 9.

On reaching this temperature, the preheated nitrate and potassium carbonate solutions G and F respectively were slowly pumped simultaneously into the first reactor, while keeping a pH of 8,5–9 and a stirring speed of 250 rpm. An immediate precipitation occurred and after a residence time of about 15 minutes, the slurry was allowed to overflow from the first reactor to the second reactor. The aging time of the crystallized catalyst precursor in the second reactor was about 1 hour. The overflow from reactor 50 containing the slurried and aged precipitate was continuously filtered and washed using warm demineralized water (40° C.) in the Buchner funnel 76. The filter cake comprising the final catalyst precursor had a grey colour.

The filter cake was then dried overnight, in air, at a temperature of 90° C., and it was finally calcined at 350° C. for 4 hours. This procedure converted the hydrated hydroxycarbonate precursor to a catalyst comprising optimally divided mixed oxides and spinells.

Tests carried out on small samples of the dried but not yet calcined precursor by means of X-ray power diffraction revealed the formation of a homogeneous, highly-crystalline, precursor of the hydrotalcite type, $Cu_2Zn_4Cr_2(OH)_{16}Co_3.4H_2O$ in a highly pure form, ie without any measurable content of impurities such as an orthorhombic binary aurichalcite-like phase, $(Cu:Zn)_5(OH)_6(CO_3)_2$, a monoclinic hydrozincite-like phase of the same chemical composition but with a differing amount of crystal water, and/or a malachite-like phase, $(Cu:Zn)_2(OH)_2CO_3$. Absence of such impurities indicates high purity hydrotalcite-like phase in the precursor, which after careful calcination gives a catalyst with resultant good thermal stability and other catalytic properties.

In the X ray diffractogramms of the calcined catalyst the formation of a copper-zinc-chromite spinell phase of a very small crystallite size (<3 nm) was identified.

The BET surface area of the calcined catalyst was 134 $m^2/g$.

The calcined catalyst was then pressed into tablets, crushed and sieved to a particle size of 300–350 μm (microns).

A final catalyst for the production of higher alcohols was obtained by incipient wetness impregnation of the calcined catalyst with the required quantity of an aqueous solution of cesium formate to give 3% by mass cesium, based on the total catalyst mass.

EXAMPLE 2

Preparation of Catalyst B

A precursor was prepared in a continuous process as indicated in FIG. 1, ie similar to the one used for preparing the catalyst A (Example 1), with the difference that the first reactor 12 was a 200 ml tubular cell reactor of 500 mm length. There was strict control of temperature, pH and stirring speed. The residence time in reactor 12 was very well controlled. The residence time in reactor 12 was 2 minutes and the aging time in reactor 50 was 60 minutes. Otherwise, the preparation was the same as in the case of catalyst A.

As in Example 1, in the X-ray diffractogramm of the calcined catalyst B the formation of a copper-zinc-chromite spinell phase of a very small crystallite size (<3 nm) was identified.

The BET surface area of the calcined catalyst was 140 $m^2/g$.

The further handling and impregnation of the calcined catalyst was identical to that of catalyst A.

EXAMPLE 3

Preparation of Catalyst C

The preparation of the catalyst was identical to that of Example 2, apart therefrom that, instead of the solution of 1M chromium nitrate, a corresponding solution of aluminium nitrate was added to the nitrates solutions of copper, zinc, zirconium and manganese to form the solution G. Additionally, the calcination temperature was 450° C.

Tests carried out on small samples of the dried but not yet calcined precursor by means of X ray power diffraction revealed the formation of a homogeneous, highly-crystalline, precursor of the hydrotalcite type, $Cu_2Zn_4Al_2(OH)_{16}CO_3.4H_2O$ in a highly pure form, ie without any measurable content of other crystalline hydroxycarbonates. The crystals formed using this method were much larger than those obtained in Examples 1 and 2.

In the X-ray diffractogramm of the calcined catalyst the formation of a copper-zinc-aluminium spinell phase of a very small crystallite size (<3 nm) was identified.

The BET surface area of the calcined catalyst was 132 $m^3/g$.

The further handling and impregnation of the calcined catalyst was identical to that of catalyst A.

EXAMPLE 4

Preparation of Catalyst D

This catalyst was prepared using a batch process.

3100 ml of an aqueous 10% solution of potassium carbonate, $K_2CO_3$, were added to an 8 l well stirred reactor (reactor I) which was equipped with a thermostated double mantle. Additionally, 500 ml of a 10% potassium acetate solution were added to the same reactor as a buffer. The reactor contents were heated to a temperature of 50° C.

A separate mixture comprising 345 ml of a 1,0M solution of chromium nitrate, $Cr(NO_3)_3.9H_2O$, containing 18 g Cr; 678 ml of a 0,5M solution of copper nitrate, $Cu(NO_3)_2 6H_2O$, containing 21,6 g Cu; 894 ml of a 0,5M zinc nitrate solution, $Zn(NO_3)_2.6H_2O$; and finally, 51,84 ml of a solution of $Mn(NO_3)_2$ containing 1,44 g Mn, was heated in a separate vessel (Reactor II) also to 50° C.

The contents of the reactor II were pumped to reactor I. The rate of addition was 100 ml/min. The pH in reactor I dropped rapidly from an initial value of 11 to a value of 8,3 and it finally stabilized at 8,5.

The aging time of the crystallized catalyst precursor in reactor I was about 1 hour. The slurry containing the aged precipitate was then filtered and washed using warm demineralized water (40° C.) in suitably arranged Buchner funnels. The filter cake comprising the final catalyst precursor had a grey colour. The formation of a homogeneous, crystalline, precursor of the hydrotalcite type, $Cu_2Zn_4Cr_2(OH)_{16}CO_3.4H_2O$ in a highly pure form, without any measurable quantities of other crystalline hydroxycarbonates was demonstrated by means of X ray power diffraction.

Calcination and further handling of the catalyst was carried out in substantially the same fashion as Catalyst A in Example 1.

After calcination, the BET surface area of the catalyst was 125 $m^2/g$.

EXAMPLE 5

Preparation of Catalyst E

The preparation of the catalyst was identical to that of Catalyst B described in Example 2 save that, instead of using a solution of $Zr(NO_3)_4$ (solution D) as the means for adding the zirconium, the latter was added using the following procedure.

Typically, a solution was prepared of the corresponding amount of high purity zirconium isopropoxide (ZIP) in isopropanol. This solution was added dropwise and under stirring into an excess of hot demineralised water (100 moles $H_2O$/ZIP). The hydrolysis temperatures used were higher than 80° C. and a basic requirement is that the addition of the alkoxide proceeds rapidly. Peptisation is effected by adding small amounts of nitric or acetic acid to the heated stirred solution. As a result of the above procedure a clear zirconium sol is obtained, which is stable for many hours. Excess water was evaporated via an extended heat treatment of the solution at 80° C.

Tests carried out on small samples of the dried but not yet calcined precursor by means of X ray power diffraction revealed the formation of a homogeneous, highly-crystalline, precursor of the hydrotalcite type, $Cu_2Zn_4Al_2(OH)_{16}CO_3 \cdot 4H_2O$ in a highly pure form, ie without any measurable content of other crystalline hydroxycarbonates. The crystals formed using this method were much larger than those obtained in Examples 1 and 2.

In the X-ray diffractogramm of the calcined catalyst the formation of a copper-zinc-aluminium spinell phase of a very small crystallite size (<3 nm) was identified.

The BET surface area of the catalyst after calcination was 124 $m^2$/g.

The further handling and impregnation of the calcined catalyst was identical to that of Catalyst A.

EXAMPLE 6

Preparation of Catalyst F

The preparation of catalyst F was carried out in two stages.

In the first stage the necessary quantities of solutions A, B and C (see preparation of catalyst A above) were measured in a suitable conical beaker so that the mass of copper, zinc and chromium in the beaker was, respectively, 18,625 g, 18,625 g and 12,415 g (Solution 1). In the same way, an aqueous solution of 10% sodium carbonate was made up by dissolving 500 g of the salt in 5 l demineralized water (solution 2). Solutions 1 and 2 were placed in a heating bath and were brought to a temperature of 60° C.

Into a 10 l stirred reactor 50 (stirring speed 300 rpm), 500 ml of a 10% sodium acetate buffer solution were added and heated to 60° C. This stirred vessel was provided with a suitable heating mantle 56, an efficient stirrer 68 and devices for measuring and controlling temperature pH, and stirring speed. On reaching temperature (60° C.) solutions 1 and 2 were slowly pumped into the reactor, keeping a pH of 8,50, and forming at once a light grey precipitate. After finishing the precipitation (55 min) the catalyst precursor was aged in its mother liquor for another 60 min. The precipitate was then transferred on to a filter apparatus (not shown) where it was filtered and washed using 6 l of warm demineralised water, transferred once again into the stirred reactor 50 and the temperature again adjusted to 60° C.

In the second stage, 200 ml demineralised water was added to the cell reactor 12 and heated to 60° C.

Separately, two solutions 3 and 4 were prepared. Solution 3 contained 55 ml of a 0.5M solution of $Mn(NO_3)_2$ corresponding to 2,23 g of Mn and 15 ml of a commercial zirconia sol corresponding to 2,25 g Zr. The solution was diluted to 250 ml. Solution 4 comprised a 10% ammonia solution which was made by diluting a commercial 25% ammonia solution with demineralised water.

Solutions 3 and 4 were placed in a heating bath and after the temperature reached 60° C. they were slowly pumped into the energetically stirred (500 rpm) cell reactor 12 at a pH of 8. The cell reactor was connected in cascade with the 10 l reactor 50 and the formed zirconia-mangania gel allowed to overflow into that reactor where it was intimately mixed with the Cu-Zn-Cr precipitate of stage 1. The two precipitates were allowed to age for another 30 min whereafter they were filtered, washed, dried and calcined as described in Example 1.

The composition of the final catalyst in terms of atomic ratios of the elements included was as follows:

$$Cu_{1.23}Zn_{1.18}Cr_{1.0}Zr_{0.1}Mn_{0.17}$$

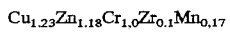

and the BET surface area was 120 $m^2$/g.

EXAMPLE 7

Preparation of Catalyst G

The preparation of catalyst G was carried out by means of sequential co-precipitation in three stages. In stage I (which is carried out first) a lanthana-stabilized zirconia matrix is formed. Stage II comprises the formation of a chromia-doped aurichalcite crystalline phase by co-precipitation of copper, zinc and chromium nitrates in strictly defined ratios. Finally, in stage III the precipitates of stages I and II are intimately intermixed and the final catalyst precursor is formed.

19,01 g copper nitrate were dissolved in 80 ml demineralised water in a 400 ml vessel, ie in a first vessel. In a separate second vessel, 46,61 g of zinc nitrate tetrahydrate were dissolved in 180 ml demineralised water. Further, 15,4 g chromium nitrate were dissolved in 40 ml demineralised water in a third vessel. Solution A (total volume: approximately 500 ml) was made up by adding the contents of the second and the third vessels into the first vessel. Solution B was prepared by addition of 130 g of NYACOL (trade name) 20% colloidal zirconia solution to 420 ml demineralised water under stirring, and the subsequent addition of 40 ml 65% $HNO_3$ for peptization. Further, 4,86 g of lanthanum nitrate were dissolved in 40 ml demineralised water, and added to the zirconia solution. As a result of the above procedure a clear zirconia-lanthana sol is obtained, which is stable for many hours. Solution C was made up by dissolving 100 g of potassium carbonate in 2 liter demineralised water. Solution D was made up by dissolving 50 g of potassium hydroxide in 1 liter demineralised water. Finally, Solution E was made up by dissolving 100 g of potassium acetate in 1000 ml demineralised water.

Stage I:

Solutions B and D were placed in a heating bath and were brought to a temperature of 40° C. Into a 6 liter stirred reactor, 200 ml of Solution E were added and heated to 40° C. This stirred vessel was provided with a suitable heating mantle, an efficient stirrer and devices for measuring and controlling temperature, pH and stirring speed. On reaching temperature, Solutions B and D were slowly pumped into the reactor, under vigorous stirring, maintaining a pH of 9,00, with a precipitate forming at once. After the addition was completed, the precipitate was aged in the mother liquor for an additional 2 hours at this temperature.

Stage II:

Into a 4 liter stirred reactor, 300 ml of Solution E were added and heated to 60° C. This stirred vessel was provided with a suitable heating mantle, an efficient stirrer and devices for measuring and controlling temperature, pH and stirring speed. On reaching temperature, Solutions A and C were slowly pumped into the reactor, under stirring, maintaining a pH of 8,00, with a precipitate forming at once. After the addition was completed, the precipitate was aged in the mother liquor for additional 30 minutes at this temperature. At this stage a small sample was taken and, after drying for 16 hours at 80° C., it was shown by means of XRD analysis to consist mainly of chromia-doped aurichalcite.

Stage III:

The 4 liter reactor of stage II was connected with the 6 liter reactor of stage I, and the formed chromia-doped copper-zinc hydroxycarbonate slurry was pumped into the reactor of stage I, where it was intimately mixed with the zirconia-lanthana precipitate of stage I. The temperature was increased to about 80° C. within a short period of time, and the mixture of the two precipitates was allowed to age for another 30 minutes at this temperature. Thereafter, the homogeneous slurry was filtered, and the filtrate washed with 5 liters of warm demineralised water, dried (80° C. for 16 hours) and calcined (350° C. for 3 hours, using a temperature programme of 1,5° C./min, in similar fashion to that of Example 1).

The composition of the final catalyst in terms of atomic ratios of the elements included was as follows:

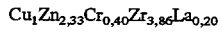

$Cu_1Zn_{2,33}Cr_{0,40}Zr_{3,86}La_{0,20}$

The DET surface area of the catalyst G was found to be: 135 m²/g.

EXAMPLE 8

Preparation of Catalyst H

The preparation of catalyst G is very similar to that of catalyst F, ie it is carried out by means of sequential co-precipitation in three stages. In stage I an india-stabilized zirconia matrix is formed. Stage II comprises the formation of a mangania-doped aurichalcite crystalline phase by co-precipitation of copper, zinc and manganese nitrates in strictly defined ratios. Finally, in stage III the precipitates of stages I and II are intimately intermixed and the final catalyst precursor is formed.

19,97 g copper nitrate were dissolved in 80 ml demineralised water in a 400 ml vessel, ie in a first vessel. In a separate second vessel, 48,97 g of zinc nitrate tetrahydrate were dissolved in 180 ml demineralised water. Further, 8,45 g manganese nitrate were dissolved in 40 ml demineralised water in a third vessel. Solution A (total volume: approximately 500 ml) was made up by adding the contents of the second and the third vessels into the first vessel. Solution B was prepared by addition of 48,16 g zirconyl nitrate and 3,40 g of indium nitrate to 500 ml demineralised water under intensive stirring. Solution C was made by dissolving 100 g of potassium carbonate in 2 liter demineralised water. Solution D was made by dissolving 50 g of potassium hydroxide in 1 liter demineralised water. Finally, Solution E was made by dissolving 100 g of potassium acetate in 1000 ml demineralised water.

The stage-wise procedure of preparation of this catalyst sample was identical with that described in Example 7.

The composition of the final catalyst in terms of atomic ratios of the elements included was as follows:

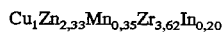

$Cu_1Zn_{2,33}Mn_{0,35}Zr_{3,62}In_{0,20}$

The BET surface area of the catalyst H was found to be: 142 m²/g.

Figure 2:
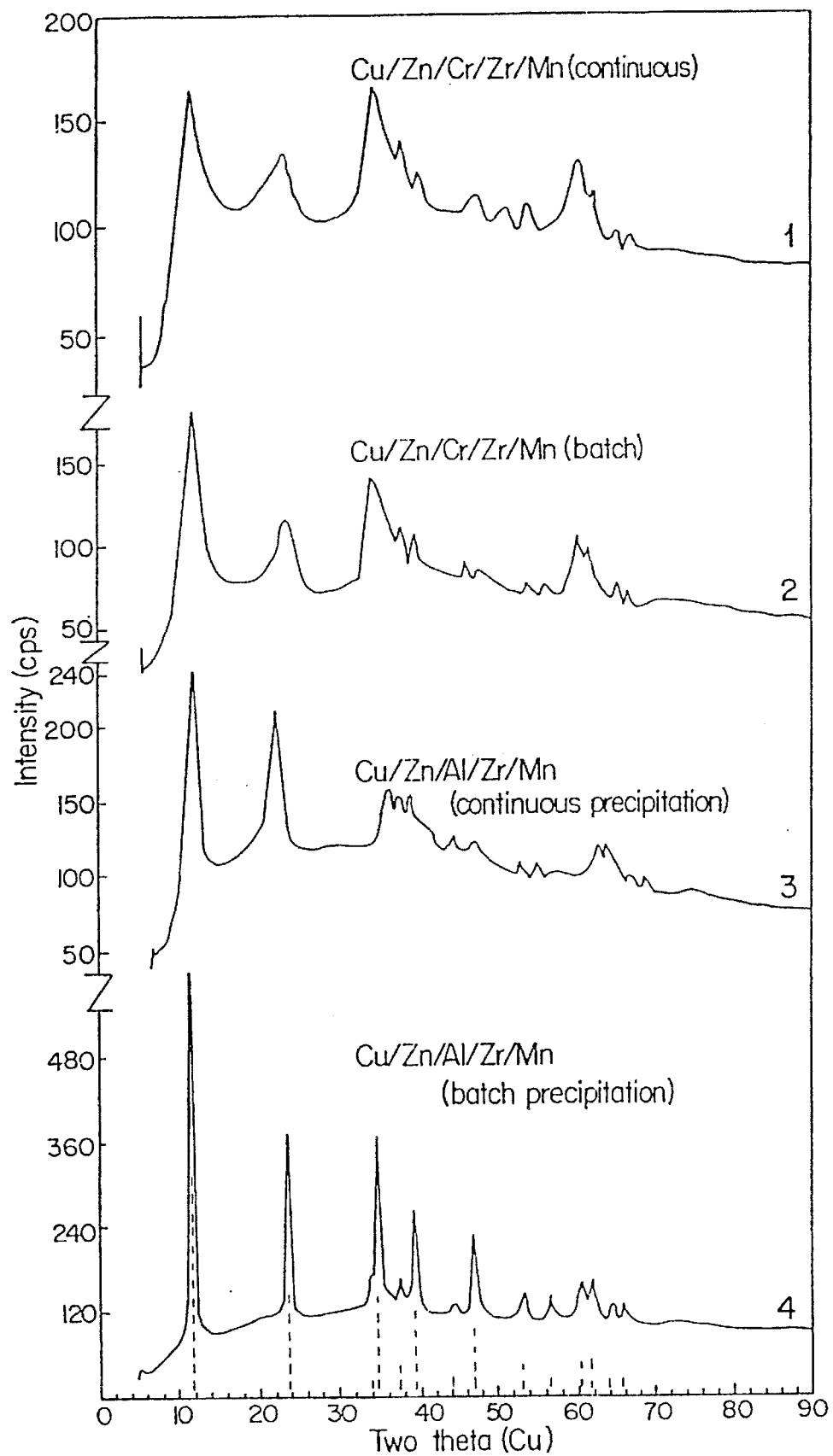
FIG. 2 shows X-ray diffraction powder patterns of catalyst precursors (dried at 90° C.) obtained in the apparatus of FIG. 1.
Figure 3:
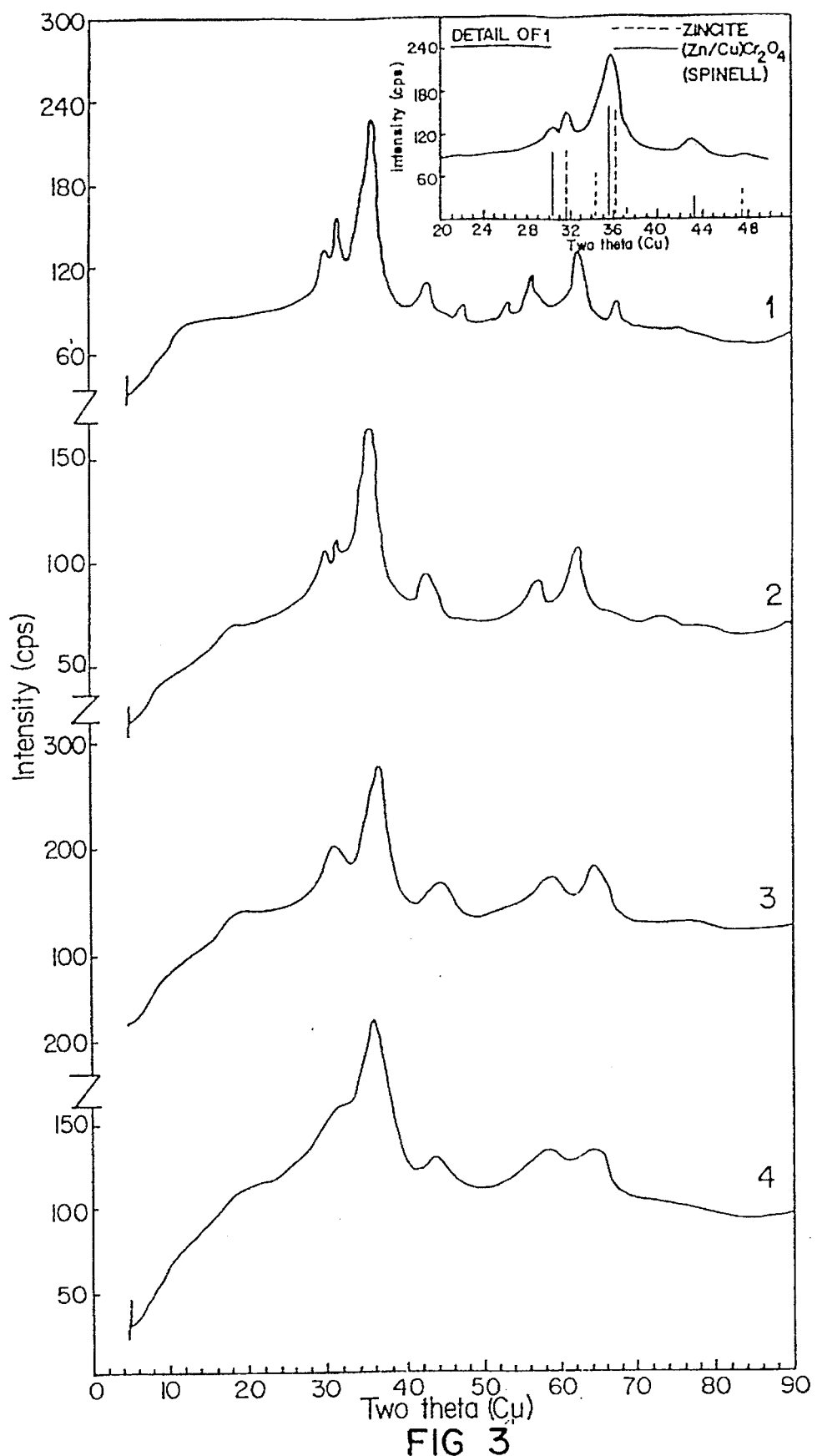
FIG. 3 shows X-ray diffraction powder patterns of catalysts obtained by calcination (350° C., 4 hours) of the precursors of FIG. 2.
Figure 4:
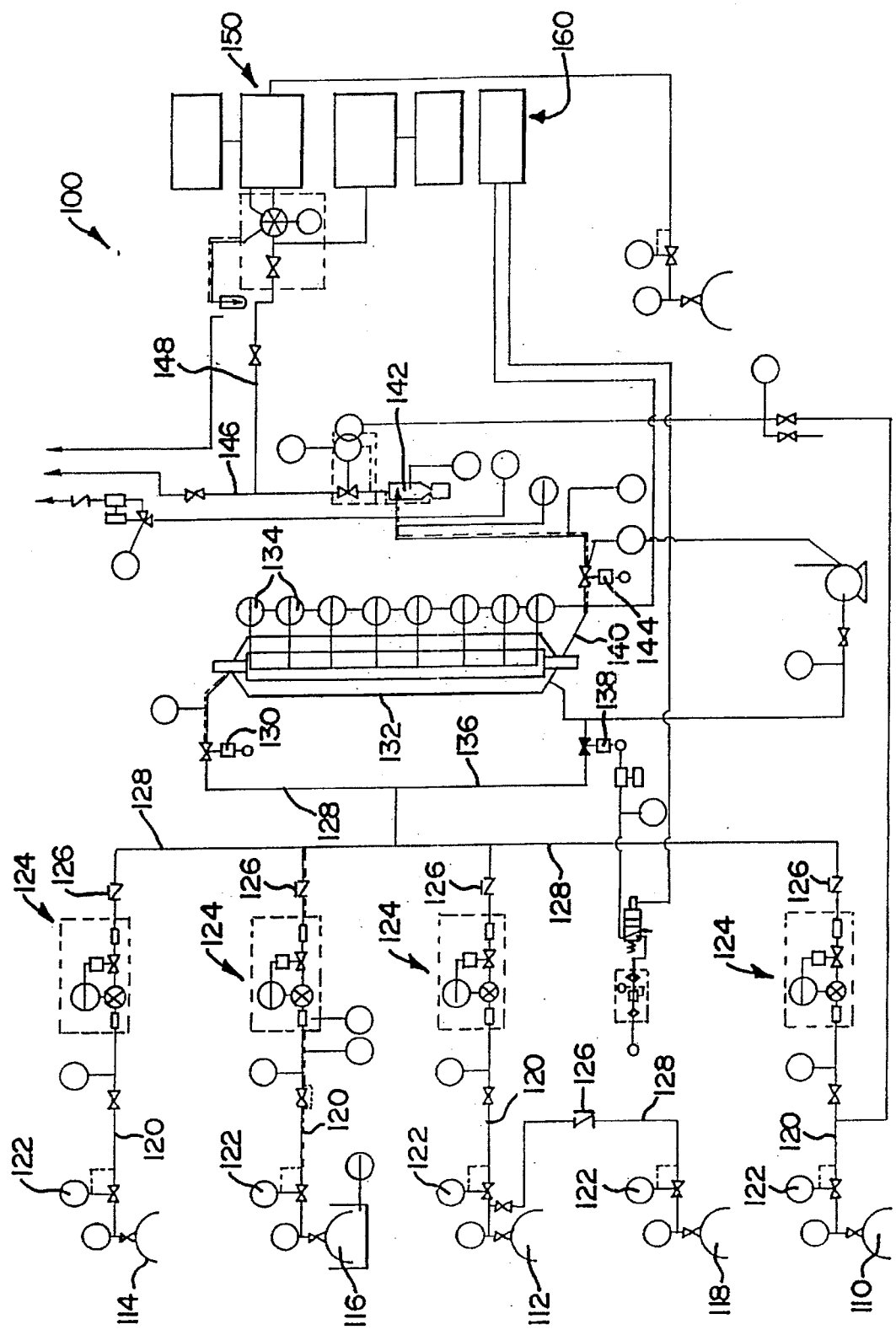
FIG. 4 shows, schematically, experimental apparatus for testing higher alcohol synthesis catalysts according to the invention, in the production of higher alcohols according to the invention.

Some of the catalysts of Examples 1 to 8 were then tested using the experimental apparatus 100 shown schematically in FIG. 2, and using the procedure described hereunder. This procedure thus simulates a process according to the invention for producing higher alcohols using the catalysts of the invention.

The experimental apparatus 100 comprises pressurized cylinders 112, 114, 116, 118 and 110 containing, respectively, Co, $H_2$, $CO_2$, $N_2$ and inert gas such as Argon.

From the cylinder 110 leads a flow line 120, fitted with a pressure regulator 122, a flow control arrangement 124, and a non-return valve 126. The flow line 126 leads into a common flow line 128.

Similar flow lines 120, pressure controllers 122, flow control arrangements 124 and non-return valves 126 lead from each of the cylinders 112, 114 and 116. The flow line 120 leading from the cylinder 116 is provided with heating means such as an electric heating tape.

From the cylinder 118 leads a flow line 128 fitted with a pressure controller 122 and a non-return valve 126. The flow line 128 leads into the flow line 120 leading from the cylinder 112.

The flow line 128 is fitted with a flow control valve 130 and leads into the top of a reactor 132, fitted with thermocouples 134.

A branch 136 leads from the flow line 128 to the bottom of the reactor 132, and is fitted with a flow control valve 138. The by-pass 136 is used for analysing the feed gas and establishing a measure of the conversion over the catalyst.

A heated flow line 140 leads from the bottom of the reactor 132 to a collecting vessel 142. The flow line 140 is fitted with a control valve 144.

A flow line 146 leads from the vessel 142, and can be used for venting the contents of the vessel 142. However, a flow line 148 leads from the flow line 146 to a gas chromatograph arrangement, generally indicated by reference numeral 150.

The installation 100 also includes a pressure control system, generally indicated by reference numeral 160, for controlling the apparatus 100.

In use, each of the catalysts tested was impregnated as hereinbefore described with particular reference to Example 1 prior to a quantity thereof being charged to the reactor 132. In each case a synthesis gas composition as hereinafter described, was fed to the reactor 132, from the cylinders 110 to 118, and the product gas from the reactor analyzed using the gas chromatography arrangement 150. The results obtained are set out in Tables 2, 3, 4 and 5.

TABLE 2

TEST UTILIZING CATALYST A
Reaction Temperature: 325° C., Pressure: 10 MPa, GHSV: 4000, $H_2/CO:1$, 1% $CO_2$

| COMPOUND | SELECTIVITY (Mass-%) | SPACE-TIME-YIELD ('STY') g/Kg$_{cat}$ h |
|---|---|---|
| Methane | 4,27 | 18,83 |
| Ethene + Ethane | 0,48 | 4,11 |
| Propene + Propane | 0,39 | 2,10 |
| Methanol | 29,33 | 129,22 |
| Dimethyl Ether | 6,88 | 30,32 |
| 1-Butene | 0,11 | 0,50 |
| n-Butane | 0,05 | 0,22 |
| Ethanol | 17,91 | 78,88 |
| Propan-2-ol | — | — |
| 1-Pentene | 0,10 | 0,44 |
| n-Pentane | 0,03 | 0,12 |
| 2-Methylpropan-2-ol | 2,15 | 9,47 |
| Propan-1-ol | 13,92 | 61,33 |
| 1-Hexene | 0,01 | 0,05 |
| Butan-2-ol | 0,35 | 1,56 |
| n-Hexane | 0,08 | 0,34 |
| 2-Methylpropan-1-ol (Isobutanol) | 16,71 | 73,65 |
| Butan-1-ol | 2,14 | 9,43 |
| Pentan-1-ol | 1,03 | 4,54 |
| Pentanols | 1,41 | 6,23 |
| Methylbutanols | 4,26 | 13,72 |

Carbon Monoxide Conversion (C-Mol %) 24,31
Total Alcohol Selectivity (mass-%) >78,85 (STY: 347,47 g/gh)
Total STY 440,63 g/gh

TABLE 3

TEST UTILIZING CATALYST B
Reaction Temperature: 325° C., Pressure: 10 Mpa, GHSV: 8000, $H_2/CO:1$, 1% $CO_2$

| COMPOUND | SELECTIVITY (Mass-%) | SPACE-TIME-YIELD ('STY') g/Kg$_{cat}$ h |
|---|---|---|
| Methane | 3,48 | 32,36 |
| Ethene + Ethane | 0.76 | 9,01 |
| Propene + Propane | 0,39 | 5,02 |
| Methanol | 43,34 | 168,99 |
| Dimethyl Ether | 5,60 | 7,98 |
| 1-Butene | 0,10 | 2,65 |
| n-Butane | 0,04 | 1,54 |
| Ethanol | 14,59 | 94,21 |
| Propan-2-ol | — | — |
| 1-Pentene | 0,08 | 0,65 |
| n-Pentane | 0,02 | 0,11 |
| 2-Methylpropan-2-ol | 1,75 | 11,32 |
| Propan-1-ol | 11,34 | 68,54 |
| 1-Hexene | 0,01 | 0,05 |
| Butan-2-ol | 0,29 | 2,57 |
| n-Hexane | 0,06 | 0,34 |
| 2-Methylpropan-1-ol | 13,62 | 117,01 |

TABLE 3-continued

TEST UTILIZING CATALYST B
Reaction Temperature: 325° C., Pressure: 10 Mpa, GHSV: 8000, $H_2/CO:1$, 1% $CO_2$

| COMPOUND | SELECTIVITY (Mass-%) | SPACE-TIME-YIELD ('STY') g/Kg$_{cat}$ h |
|---|---|---|
| (Isobutanol) | | |
| Butan-1-ol | 1,74 | 11,34 |
| Pentan-1-ol | 0,83 | 4,78 |
| Pentanols | 1,15 | 6,92 |
| Methylbutanols | 3,46 | 12,29 |

Carbon Monoxide Conversion (C-Mol %) 17,36
Total Alcohol Selectivity (mass-%) >90,72 (STY: 505,92 g/gh)
Total STY 557,68 g/gh

TABLE 4

TEST UTILIZING CATALYST C
Reaction Temperature: 325° C., Pressure : 10 MPa, GHSV: 4000, $H_2/CO:1$, 5% $CO_2$

| COMPOUND | SELECTIVITY (Mass-%) | SPACE-TIME-YIELD ('STY') g/Kg$_{cat}$ h |
|---|---|---|
| Methane | 1,38 | 5,58 |
| Ethene + Ethane | 1,04 | 4,18 |
| Propene + Propane | 0,56 | 2,25 |
| Methanol | 56,07 | 225,94 |
| Dimethyl Ether | 2,49 | 10,04 |
| 1-Butene | 0,13 | 0,51 |
| n-Butane | 0,05 | 0,22 |
| Ethanol | 7,41 | 29,88 |
| Propan-2-ol | — | — |
| 1-Pentene | 0,11 | 0,44 |
| n-Pentane | 0,03 | 0,12 |
| 2-Methylpropan-2-ol | 0,80 | 3,22 |
| Propan-1-ol | 8,84 | 35,62 |
| 1-Hexene | 0,01 | 0,05 |
| Butan-2-ol | 0,39 | 1,56 |
| n-Hexane | 0,08 | 0,34 |
| 2-Methyl-propan-1-ol | 11,28 | 45,47 |
| Butan-1-ol | 1,62 | 6,52 |
| Pentan-1-ol | 0,91 | 3,67 |
| Pentanols | 1,13 | 4,56 |
| Methylbutanols | 3,06 | 12,32 |
| Unidentified | 2,60 | 10,50 |

Carbon Monoxide Conversion (C-Mol %) 16,54
Total Alcohol Selectivity (mass-%) >90%
Total STY 402,99

TABLE 5

SYNTHESIS OF METHANOL AND HIGHER ALCOHOLS

Reaction Conditions

| | | | |
|---|---|---|---|
| Temperature (°C.): | 325,00 | Reactor: | Integral (10 g catal.) |
| Pressure (MPa): | 10,00 | | |
| GHSV (ml/g/h): | 8000,00 | (mol/g/h): | 133,95 |

Gas Composition

| | |
|---|---|
| Carbon monoxide (Vol-%): | 47,00 |
| Carbon monoxide (Vol-%): | 1,00 |
| Hydrogen (Vol-%): | 47,00 |
| Argon (Vol-%): | 5,00 |

| COMPOUND | MOLECULAR WEIGHT | SELECTIVITY (Mol-%) | SELECTIVITY (Mass-%) | SPACE-TIME-YIELD (g/kg/h) |
|---|---|---|---|---|
| Methane | 16,00 | 6,95 | 3,50 | 22,37 |
| Ethene + Ethane | 28,00 | 4,20 | 2,88 | 17,47 |
| Propene + Propane | 40,00 | 1,18 | 1,15 | 7,37 |
| Methanol | 32,00 | 58,54 | 45,81 | 292,63 |
| Dimethyl Ether | 46,00 | 2,31 | 2,60 | 16,60 |
| Butene-1 | 56,00 | 0,06 | 0,08 | 0,52 |
| n-Butane | 58,00 | 0,56 | 0,78 | 4,98 |
| Ethanol | 46,00 | 4,53 | 5,10 | 32,55 |
| Methyl-formate | 60,00 | 0,95 | 1,39 | 8,90 |
| Methyl-ethyl-ketone | 72,00 | 0,67 | 1,18 | 7,54 |
| Propan-1-ol | 60,00 | 3,97 | 5,82 | 37,21 |
| Methyl-acetate | 88,00 | 0,68 | 1,46 | 9,35 |
| Methyl-2-propan-1-ol | 74,00 | 5,81 | 10,51 | 67,16 |
| Butan-1-ol | 74,00 | 1,06 | 1,92 | 12,25 |
| Methyl-2-butan-1-ol | 88,00 | 1,58 | 3,40 | 21,72 |
| Pentan-1-ol | 88,00 | 0,55 | 1,18 | 7,56 |
| Methyl-2-pentan-1-ol | 102,00 | 0,59 | 1,47 | 9,40 |
| Hexan-1-ol | 102,00 | 0,12 | 0,30 | 1,91 |
| Methyl-2-hexan-1-ol | 116,00 | 1,05 | 3,01 | 19,21 |
| Other | 100,00 | 2,64 | 6,46 | 41,24 |
| Carbon dioxide | | | | 495,00 |
| CO CONVERSION (C-Mol-%): | | (*) RELATIVE: 21,60 | ABSOLUTE (Int Std): 22,15 | |
| TOTAL ALCOHOL SELECTIVITY (Mass-%): | | 78,52 | | |
| MeOH/TOTAL ALCOHOLS RATIO: | | 0,58 | | |

(*) without conv. to $CO_2$

TABLE 6

TESTS UTILIZING CATALYSTS G AND H
Comparative results of the synthesis of lower alcohols over catalysts G and H (impregnated with 1% Cs by mass)
Reaction conditions: (Press.: 10 MPa, GHSV; 8000 h$^{-1}$
Temp.: 325° C., syngas: CO = 62 mol-%, $H_2$ = 31 mol-%, $CO_2$ = 2 mol-%, Ar = 5 mol-%; results after 54 h onstream)

| | CATALYST G | CATALYST H |
|---|---|---|
| CO Conversion (C-mol-%) | 26,21 | 27,73 |
| Total Alcohol Selectivity (mass-%) | 80,75 | 82,21 |
| Methanol Space-Time-Yield (g/kg$_{cat}$/h) | 163,21 | 157,50 |
| Isobutanol Space-Time-Yield (g/kg$_{cat}$/h) | 72,84 | 87,55 |
| MeOH/ROH ratio | 0,51 | 0,48 |

It can thus be seen that with catalysts according to the invention efficient simultaneous synthesis of methanol and isobutanol, by mens of CO hydrogenation, can be effected.

It is also clear from the tests conducted that the precursors of these catalysts have homogeneous highly crystalline structures of the hydrotalcite type such as $Cu_2Zn_4Cr_2(OH)_{16}CO_3.4H_2O$, as hereinbefore described.

It is believed that the manganese, which may exist as $Mn^{2+}$ or $Mn^{3+}$ is incorporated into the crystal structure.

It was further found that the zirconium, whether added to the catalyst precursor as a nitrate solution, such as in Example 1, or in colloidal form as a sol, such as in Example 5, resulted in a substantial improvement in the textural and thus overall catalytic properties of the resultant catalysts. For example, the specific surface area and the pore volume increased dramatically, distribution became much more homogeneous, and the final catalyst activity was much higher, as compared to catalysts not containing zirconium, such as the catalyst of Example 4. The tests also show that zirconium containing catalysts promote formation of branched $C_4$ hydrocarbons when used for the production of higher alcohols.

The Applicant is aware that lower alcohols, ie methanol and ethanol, are used extensively in the fuel industry. Firstly, ethanol can be used directly as an additive to gasoline or petrol to provide gasoline/ethanol blends which have acceptable water tolerance and volatility, as well as octane numbers which are higher than those of the base gasoline. However, such mixtures result in increased corrosion of vehicle engine parts, thus making it necessary to utilize in such mixtures also corrosion inhibiting compounds.

When it is attempted to use methanol on its own as a blending agent with gasoline, this presents problems as methanol has too high a blending vapour pressure. This then requires the co-use of a higher alcohol such as tertiary butyl alcohol or isobutanol as a co-solvent, in order to minimize the phase separation with water and to have acceptable volatility properties. In such case, the higher the molecular weight of the co-alcohol which is used as co-solvent, the more effective is its performance.

In addition, methanol and ethanol can be converted to methyl-tertiary-butyl-ether (MTBE) or ethyl-tertiary-butyl-ether (ETBE) which can be used as octane extenders in gasoline, thereby avoiding the need to prepare gasoline/alcohol mixtures. In particular, MTBE has already replaced or is rapidly replacing sulphur based additives, and its importance is growing because of the limitations of the aromatics and alcohol levels permitted in gasoline. Aromatics and alcohols have high octane ratings, but exhibit problems as regards exhaust pollution and their propensity for causing corrosion in vehicle engines, hence the limitations being imposed on the use thereof. By utilizing MTBE and ETBE as octane enhancers and/or oxygenated fuel additives, gasoline can be reformulated in such a way as to minimize the emission of carbon monoxide and unburnt hydrocarbons in automobile exhaust gases.

However, the conversion of methanol and/or ethanol to MTBE and/or ETBE respectively, requires an equimolar amount of isobutene as is evident from the following reactions:

| | |
|---|---|
| (1) $CH_3OH + (CH_3)_2-C=CH_2$ | $CH_3-O-C-(CH_3)_3$ |
| Methanol Isobutene | MTBE |
| (2) $CH_3CH_2OH + (CH_3)_2-C=CH_2$ | $CH_3CH_2-O-C-(CH_3)_3$ |
| Ethanol Isobutene | ETBE |

It is thus necessary not only to have a ready source of methanol or ethanol, which can easily be synthesized from synthesis gases comprising hydrogen and carbon oxides, but also a ready source of isobutene. Isobutene can be obtained from petrochemical sources such as the $C_4$ stream from steam cracking of petroleum feedstocks, after butadiene extraction. Alternatively, it can be obtained from the $C_4$ stream from catalytic crackers, which stream also contain some isobutene. However, these sources do not provide sufficient isobutene at an attractive cost.

An alternative source of isobutene is field butane streams, such as those produced in the petrochemical industry, and which contain normal butane. n-Butane can be transformed into isobutene by means of isomerization to isobutane and subsequent dehydrogenation to isobutene. However, this route is also unattractive economically as isomerization and dehydrogenation are costly.

However, isobutene can easily be produced by dehydration of isobutanol or 2-methyl-1-propanol. The present invention thus provides a catalyst whereby not only methanol but also substantial quantities of isobutanol can be synthesized simultaneously from synthesis gas. Moreover, these compounds can be synthesized also from non-petroleum synthesis gases such as synthesis gases obtained from coal gasification or from natural gas.

The isobutanol can readily be dehydrated to isobutene at moderate reaction conditions, over an acidic catalyst. Instead, methanol/isobutanol mixtures existing in the reaction product may be reacted directly to form MTBE. Still further, ethanol and propanol are obtained as major by-products. They can then either be recycled, thereby increasing the isobutanol yield, or separated by distillation.

We claim:

1. A higher alcohol synthesis catalyst precursor, which comprises a homogeneous highly crysalline hydroxycarbonate compound containing copper, zinc, and at least one element selected from the group consisting of aluminium and chromium, the hydroxycarbonate compound having a hydrotalcite-type structure having the general formula $Cu_xZn_{(6-x)}M_2(OH)_{16}CO_3"4H_2O$ where M is Cr or Al, with the atomic ratio of [Cu+Zn]:M therein being between 2:1 and 4:1, and the atomic ratio of Cu:Zn therein being between 0.4:1 and 1.2:1; and an element from Group VIIB of the Periodic Table of Elements.

2. A higher alcohol synthesis catalyst precursor according to claim 1, wherein the atomic ratio of [Cu+Zn]:M, in respect of the hydroxycarbonate compound, is between 2.75:1 and 3.25:1, and the atomic ratio of Cu:Zn in respect thereof is between 0.5:1 and 1:1.

3. A higher alcohol synthesis catalyst precursor according to claim 1, wherein the element from Group VIIB is manganese and is present in the precursor in such an amount that the atomic ratio of [Cu+Cn+Zn]:M therein is between about 20:1 and about 44:1.

4. A higher alcohol synthesis catalyst precursor according to claim 1, which includes, in addition to the hydroxycarbonate compound and the element from Group VIIB, also an element from Group IVB of the Periodic Table of elements.

5. A higher alcohol synthesis catalyst precursor according to claim 4, wherein the element from Group IVB is zirconia and is present in the precursor in such an amount that the atomic ratio of [Cu+Zn+M]:Zr is between about 18:1 and about 34:1.

6. A higher alcohol synthesis catalyst precursor according to claim 4, wherein the element of Group VIIB and, when present, the element of Group IVB are incorporated into the crystal lattice of the hydroxycarbonate compound.

7. A higher alcohol synthesis catalyst precursor according to claim 4, wherein the element of Group VIIB and, when present, the element of Group IVB, are in the form of an amorphous phase which is in homogeneous admixture with the hydroxycarbonate compound.

8. A higher alcohol synthesis catalyst precursor according to claim 1, wherein the proportion of Cu therein, on an atomic basis and based on the atomic total of Cu, Zn, M, the element of Group VIIB and, when present, the element of Group IVB, is less than about 33%.

9. A higher alcohol synthesis catalyst precursor according to claim 1, wherein the proportion of Zn therein, on an atomic basis and based on the atomic total of Cu, Zn, M, the element of Group VIIB and, when present, the element of Group IVB, is greater than about 32%.

* * * * *